United States Patent [19]

Giter

[11] Patent Number: 4,722,829
[45] Date of Patent: Feb. 2, 1988

[54] BLOOD OXYGENATOR

[76] Inventor: Gregory D. Giter, 1-39 27th St., Fairlawn, N.J. 07410

[21] Appl. No.: 842,928

[22] Filed: Mar. 24, 1986

[51] Int. Cl.$^4$ .......................... A61M 1/14; A61M 1/34
[52] U.S. Cl. ...................................... 422/46; 165/159;
210/321.3; 210/321.4; 210/321.8; 422/48;
128/DIG. 3
[58] Field of Search ........................... 210/321.3–321.5;
422/44–48; 128/DIG. 3; 165/159

[56] References Cited

U.S. PATENT DOCUMENTS

| 3,77,384 | 12/1973 | Ruger et al. | |
|---|---|---|---|
| 3,768,977 | 10/1973 | Brumfield et al. | |
| 3,769,163 | 10/1973 | Bloomfield | |
| 3,893,926 | 7/1985 | Awad | |
| 3,989,626 | 11/1976 | Bentley et al. | 210/321.4 |
| 4,111,659 | 9/1978 | Bowley | 210/321.5 |
| 4,342,723 | 8/1982 | Sado et al. | 422/48 |
| 4,351,797 | 9/1982 | Bellhouse et al. | 422/48 |

Primary Examiner—Michael S. Marcus
Attorney, Agent, or Firm—Ostrolenk, Faber, Gerb & Soffen

[57] ABSTRACT

A mass/heat exchange device for use as blood oxygenator, dializer, heat exchanger and the like, includes a rectangular or cylindrical elongated housing with first and second opposite axial ends. The interior of the housing is subdivided into three chambers, including an inlet chamber located at one axial end, an outlet chamber located at the opposite axial end and a central mass/heat transfer chamber located therebetween. A plurality of parallel tubes extend through the central chamber and connect the inlet and outlet chambers to provide passageways for treating medium to flow therebetween. The outer surface of each tube has the shape of a series of spherical lobes, connected end-to-end. Further, adjacent tubes are offset from one another to allow internesting of their lobes in a tight orderly packed manner. The treating medium, for example oxygen, flows through the tubes while a medium to be treated, for example blood, flows through the interstitial spaces between the tubes. The tight orderly packing of the tubes (a) reduces the priming volume, i.e. the total volume formed by the interstitial spaces to a mimimum while the outer surfaces of the tubes provide a large mass/heat exchange surface area; (b) enhances secondary flows within the main flow of the to-be-treated medium; and (c) provides even distribution of the to-be-treated medium within the exchanging chamber. The above-mentioned features make the apparatus very efficient in regard to its small priming volume.

23 Claims, 10 Drawing Figures

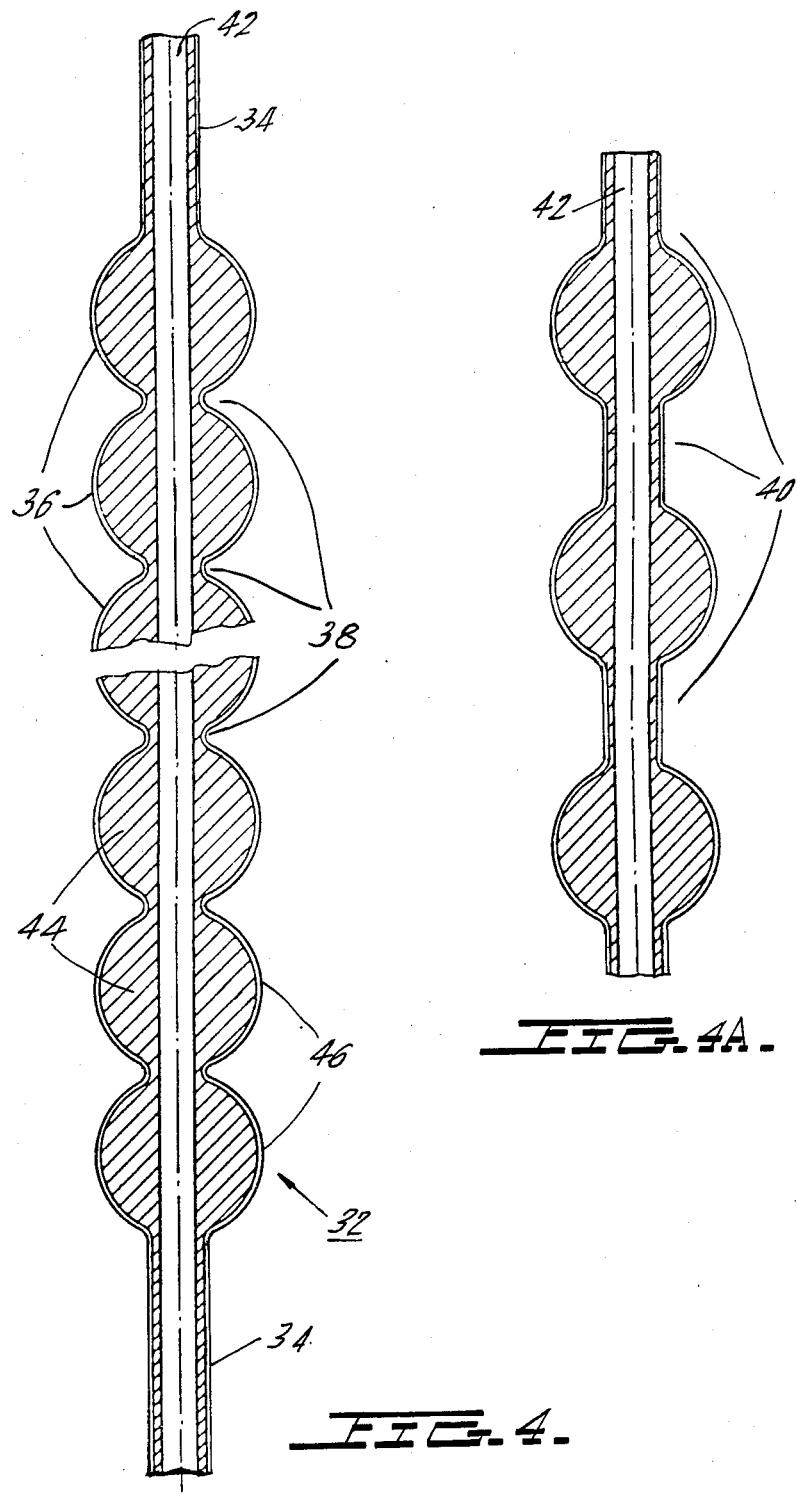

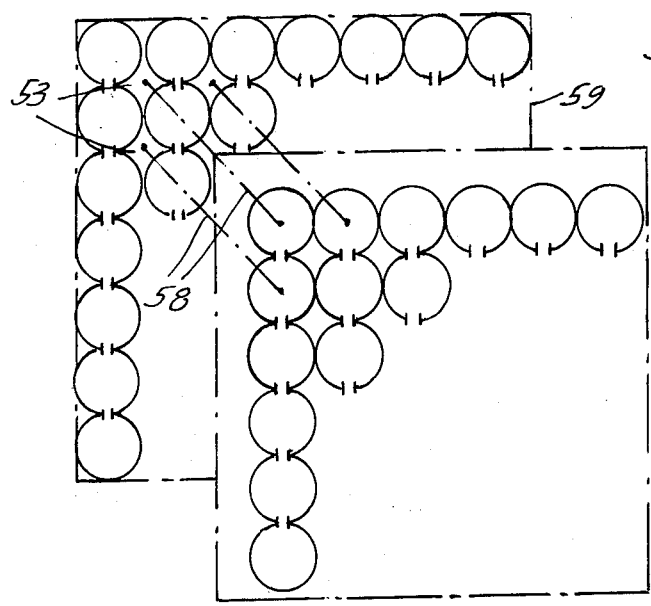
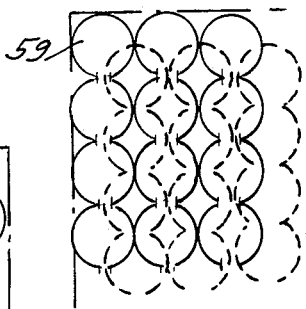
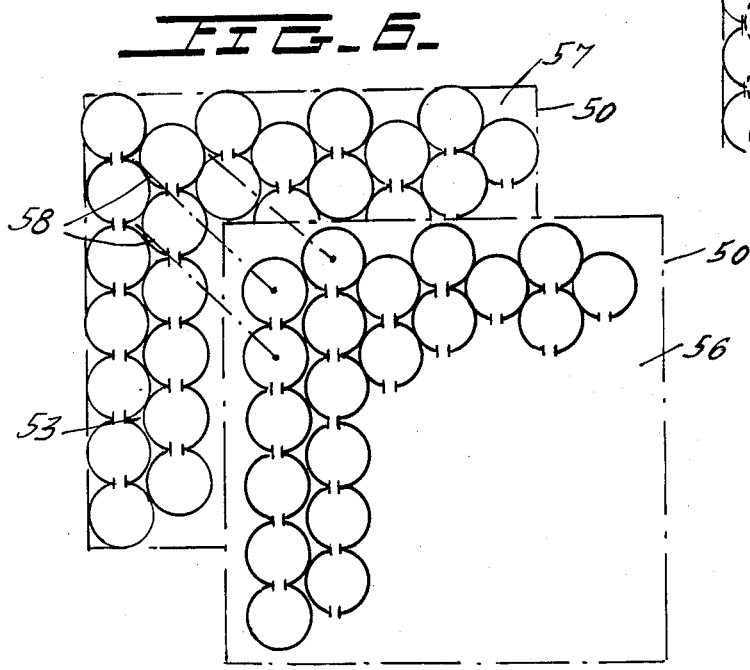

BLOOD OXYGENATOR

BACKGROUND OF THE INVENTION

The present invention relates to heat/mass exchange devices and, more particularly, to a blood oxygenator construction which optimizes the ratio of the priming volume to the exchange surface of the oxygenator, which provides even distribution of blood within the exchanging chamber and enhances secondary flows within the main blood flow.

Several concepts and approaches for constructing heat/mass transfer devices are known. One of these is based on the membrane concept. According to this concept, a treating medium, for example oxygen, and a medium to be treated, for example blood, flow across opposite surfaces of a semi-permeable membrane. The membrane keeps the main bulk of the two mediums apart but heat and/or very fine particles are nevertheless transferred across the membrane by conduction, diffusion or similar processes.

An extensive background discussion of the art which is related to the present invention is provided in U.S. Pat. No. 4,111,659 entitled "Mass and Heat Transfer Exchange Apparatus" in the name of Bowley. The contents of that patent are incorporated herein by reference.

In relation to blood oxygenators, special problems are encountered. The blood of a patient is diverted out of the body and into the oxygenator where oxygen is added to it and carbon dioxide is extracted from the blood. The blood which flows in this extra corporeal circulation path must be sufficiently oxygenated and decarbondioxidized to sustain the patient.

As a criterion of efficiency of a blood oxygenator, the ratio $K_o = Q \div V$ may be used, where Q is the flow rate through the oxygenator with given parameters and conditions such as t° equals temperature, $PO_2$ equals oxygen tension, $P_{CO2}$ is $CO_2$ tension, $\%HbO_2$ is oxygen saturation, pH of blood, as it enters and leaves the apparatus and V is the priming volume.

This formula means that the lower the priming volume (V) is of an oxygenator that provides a given amount of fully oxygenator blood at given conditions, the higher the value of $K_o$ and consequently, the more efficient it is.

High value of $K_o$ may be achieved by constructing an apparatus in which the following design features are present:

(a) Geometrically built in $K' = A \div V$, where A is the surface area of mass/heat exchange and V is the priming volume;

(b) Provisions for enhancement of secondary flows within the main to-be-treated medium flow. In the case with blood, the secondary flows must not create high shear stresses which lead to blood trauma. The secondary flows are to provide constant renewal of the membrane adjacent zero velocity layer of the blood flow; and (c) Uniform distribution of the to-be-treated medium through all and every passageway of the exchanging chamber, i.e. absence of a path of least hydraulic resistance.

The present invention is directed to a mass and heat exchange device which provides all the above mentioned design features, which make it extremely efficient.

The previously-mentioned patent to Bowley discloses an exchange apparatus which includes a large film with spherical embossment on both sides of the film. Tube-like passages criss-cross the interior of the film through which pressurized oxygen flows. The film is rolled up to form a cylindrical body which is placed in an oxygenating chamber. As pressurized oxygen is forced through the interior passages in the film, the spherical embossments jut out and create interlayer passages through which blood can flow. Oxygen and carbon dioxide flow through the semi-permeable material of which the film is made to achieve oxygenation in the conventional manner.

The apparatus described in the foregoing patent is deficient in that it does not attempt to optimize the priming volume which, in this case, is comprised of the volume between the layers of the film. Moreover, because the film is rolled up in a haphazard manner, the actual contact points between the embossed spherical protrusions of the film cannot be predicted accurately. Therefore, optimum mixing and uniform flow distribution of blood is not achieved.

U.S. Pat. No. 4,351,797 discloses a transfer member assembly which comprises an assembly of tubular conduits through which blood is passed. This device is not designed to optimize and reduce the priming volume. Similarly, U.S. Pat. No. 3,769,163 to Bloomfield discloses a blood oxygenator in which a plurality of tubes are employed. Bloomfield's device is unlike the present invention in that it does not teach the construction and advantage to be derived from the specially shaped and arranged tubes of the present invention.

Other patents which are related to the subject matter of the present invention, but more remotely than the foregoing patents, include U.S. Pat. Nos. 3,777,384, 3,893,926; and 3,768,977.

SUMMARY OF THE INVENTION

Accordingly, it is a general object of the present invention to provide a mass and heat transfer/exchange apparatus which maximizes the available exchange surface per unit priming volume in the oxygenator.

It is another object of the invention to provide a mass and heat transfer/exchange apparatus with an inherent capacity to create secondary flows within the main flow of the medium to be treated without introducing high shear stresses to the above-mentioned medium.

It is still a further object of the invention to provide a mass and heat transfer/exchange apparatus in which the flow distribution of the medium to be treated is even and uniform among all passageways throughout the exchanging chamber in absence of any path of least hydraulic resistance for the medium.

It is another object of the invention to provide a mass and heat transfer/exchange apparatus which is simple in design and economical to produce.

The foregoing and other object are realized by the transfer exchange apparatus of the present invention which comprises an enclosed, rectangular or cylindrical housing having first and second axial ends through which oxygen or another treating medium enters and exits the apparatus. A first plate near the first end of the housing defines with the housing an inlet chamber for the treating medium and a second plate located near a second end of the housing defines an outlet chamber where the medium collects prior to exiting the apparatus. A central chamber between the two plates comprises the mass/heat exchange/transfer volume.

A plurality of elongated tubes extend between the inlet and outlet chambers, passing through the central chamber. The outer surface of the tubes has the shape of a series of lobes which follow one another. The tubes abut one another and are deliberately offset lengthwise from one another so that the lobes of one tube are nested within and intermeshed with the lobes of adjacent tubes. In this manner, the interstitial spaces between the tubes, which determines the priming volume, is reduced to a minimum. At the same time, blood which enters the central chamber at one end and exits from another end thereof flows through the interstitial spaces and around the lobes, thereby secondary flows without high shear stresses are being induced, which renews the layer of the to-be-treated medium adjacent to the wall where the flow velocity otherwise would be zero to enhance the diffusion process and to eliminate clotting or other damage thereto.

With the above-described arrangement, the priming volume, i.e. the space in the central chamber which is not occupied by the tubes, is minimized while the exchange/transfer surface, i.e. the sum of all of the outer surface areas of the tubes, is maximized per unit volume in the central chamber. With this in mind, it should be apparent that although a tube construction is preferred, the objective of the invention can be realized by filling the central chamber with tightly packed lobes and by forming, straight or serpentine, conduits through them for passage of the treating medium therethrough.

For a mass exchange, the tube is constructed of microporous materials, for example plastics such as Teflon (PTFE), polypropylene and other porous plastics, as well as ceramics or ceramic metals. In the case of a blood oxygenator, to assure that only gaseous fluids flow across the surfaces of the tubes, the microporous material has a small pore size. The porous material should be hydrophobic. In the case where microporous materials of larger pore sizes are used, the tubes can be coated by a membrane of silicone or any other gas permeable material suitable for oxygenation. A hydrophobic membrane is used if the tubes are constructed of hydrophilic materials.

The mass and heat transfer/exchange apparatus of the present invention is not restricted to a blood oxygenator and may instead be used as a dialyzer or a heat exchanger or a similar device. In each case, the pores sizes of the tube materials or the membrane around the tube will be selected such that biological waste or nourishing materials can flow back and forth across the membrane but such that the bulk or aggregate remain separated from one another. In the case of dializers, the membrane will allow water and other chemicals to diffuse across its surfaces. Moreover, and specifically with reference to a heat exchanger, the tubes can be constructed of solid metals or plastic impregnated with metal.

Other features and advantages of the present invention will become apparent from the following description of preferred embodiments thereof which are described in conjunction with the following drawings.

BRIEF DESCRIPTION OF THE DRAWINGS

FIG. 4 is a longitudinal cross-section through a single tube of the present invention.

FIG. 4A is a longitudinal cross-section of a second tube embodiment.

FIG. 5 illustrates diagrammatically the manner in which the tubes are assembled into layers and the layer-to-layer internesting of the tubes in accordance with the first embodiment of the invention.

FIG. 5A depicts two superposed layers of the embodiment of FIG. 5.

FIG. 6 illustrates diagrammatically a second embodiment similar to that of FIG. 5 except for the different tube-to-tube and layer-to-layer internesting arrangement.

FIG. 6A provides a view of two superposed tube layers in accordance with the embodiment of FIG. 6.

DETAILED DESCRIPTION OF THE PREFERRED EMBODIMENTS

Figure 1:
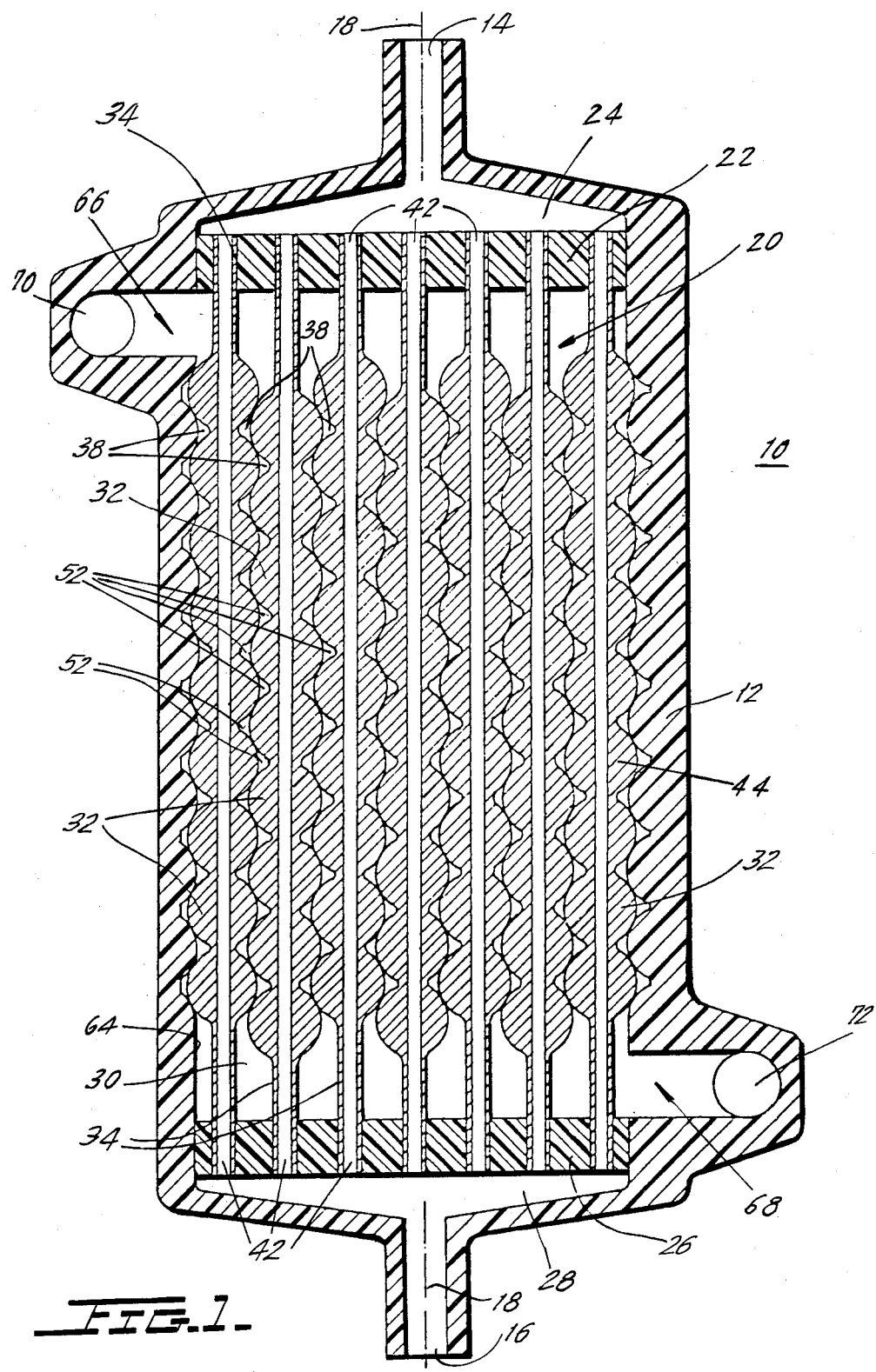
FIG. 1 is a cross-section through a first embodiment of the present invention taken along the lines 1—1 in FIG. 3.
Figure 3:
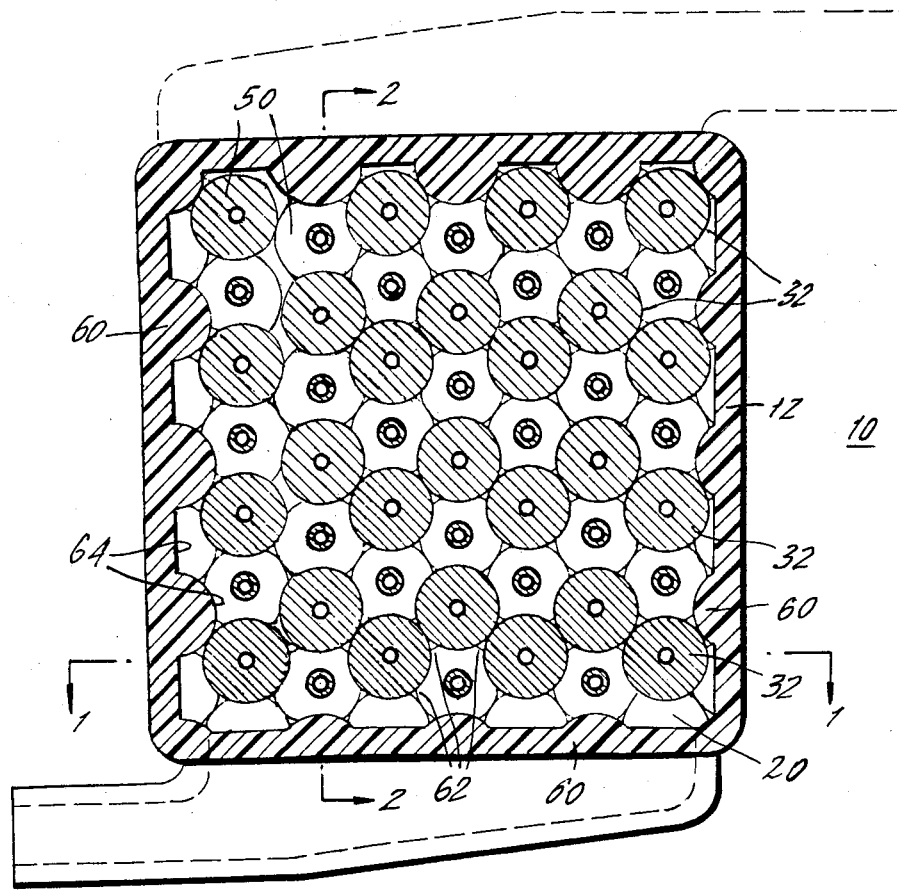
FIG. 3 is a top view in cross-section through the first embodiment of the present invention.
Figure 2:
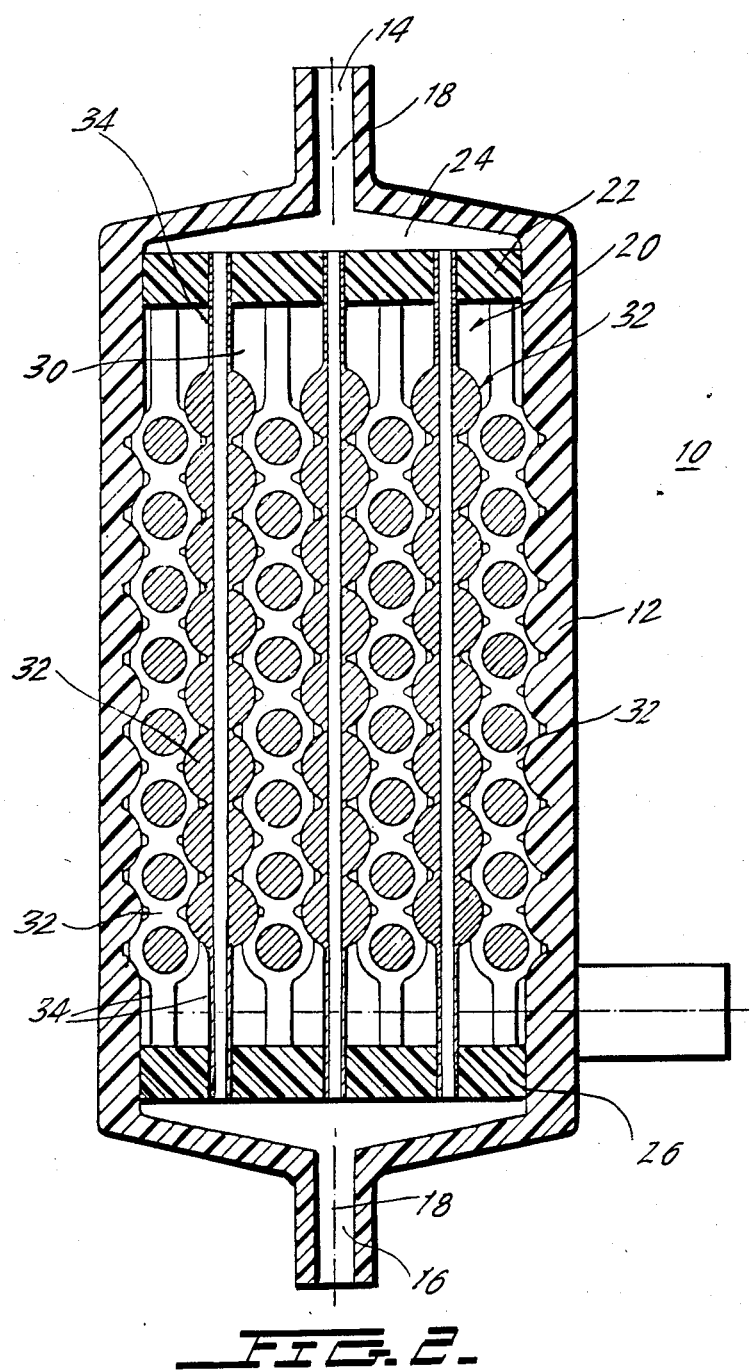
FIG. 2 is a cross-section of the first embodiment along the lines 2—2 in FIG. 3.

Referring first to FIGS. 1–3, the mass and heat transfer/exchange apparatus 10 there illustrated includes a housing 12 having a treating medium inlet 14 and a treating medium outlet 16 located at opposite longitudinal ends of the housing 12. The housing 12 extends symmetrically about longitudinal axis 18. The interior 20 of the housing 12 can be rectangular or cylindrical or other shapes. A first plate 22 within the housing 12, adjacent inlet 14, defines inlet chamber 24. Adjacent outlet 16 is a second plate 26 which defines an outlet chamber 28.

A plurality of tubular elements 32 extend between the plate 22 and 26 providing conduits 42 through which treating medium, for example oxygen, may pass from the inlet chamber 24 to the outlet chamber 28. Tubular elements 32, or tubes for short, extend through the central chamber 30 where the mass/heat transfer/exchange process takes place. Necked-down portions 34 which are formed at each end of the tubes 32 are respectively and sealingly fitted in the plates 22 and 26 to assure that the treating medium flows only in the tubes 32 and not into the central chamber 30. FIG. 2 provides a cross section through the apparatus 10 which is rotated 90° from the view provided in FIG. 1. FIG. 3 is a top view of the same apparatus 10.

The heat/mass exchange process takes place when a medium to be treated, for example blood, flows through the central chamber 30, around and between tubes 32. Through diffusion or conduction, fine particles and/or heat pass from one medium to the other thereby enabling the exchange process. As will be described below, tubes 32 are comprised of semi-permeable and/or heat conductive material.

The present invention is primarily concerned with a novel tube-shape and tube arrangement within the exchange chamber 30 which enhances the exchange process by reducing the priming volume and maximizing the total available mass exchange surface, and also by inducing secondary flows and providing even flow distribution of the to-be-treated medium flow within the apparatus.

As seen in FIG. 4, each tube 32 has an outer contour which gives it the appearance of a series of spherical lobes 36 joined to one another at lobe-to-lobe junctures 38. In a slightly modified embodiment illustrated in FIG. 4A, the tubes 32 are identical in every respect except that the lobe-to-lobe junctures 40 are stretched out to enable a tighter packing of the tubes 32 within the central chamber 30. Necked-down portions 34 at either end fit into one of the plates 22 or 26 as seen in FIGS. 1 and 2. The treating medium will flow through the conduits 42 and a portion thereof will diffuse out of the tube 32 through the semi-permeable body 44.

The material of tubes 32 is selected to suit specific types of mass/heat exchange devices, i.e. blood oxygenators, dializers, heat exchangers, etc. Typically, parameters such as porosity, heat conductivity, hydrophobic properties and biological inertness figure prominently in selecting the materials. However, in certain applications, it is advantageous to coat the body 44 with a thin membrane 46 to give it certain characteristics which the material of the body 44 lacks. An example is the hydrophobic membrane 46 which coats the body 44 of the tube which is comprised of a hydrophilic material.

The tubes 32 are tightly packed in an orderly fashion in the chamber 30 with the objective to reduce the size of the interstitial spaces 48 and hence the total priming volume which will be occupied by the medium to be treated. To this end, in accordance with a first embodiment illustrated in FIGS. 1-3 and 6-6A, pluralities of tubes 32 are combined to form flat tube layers 50 which are then assembled together as shown and described below.

In each layer 50, in accordance with the first embodiment, adjacent tubes 32 are longitudinally offset from one another so that their lobes 36 rest in each other's lobe junctures 38. The unique lobe arrangement produces a regular pattern of openings or spaces 52, each of which is defind by three surrounding lobes 36. The spaces 52 lie at the bottoms of a pattern of nests 53 in which lobes 36 from adjacent layers will be wedged.

Figure 1A:
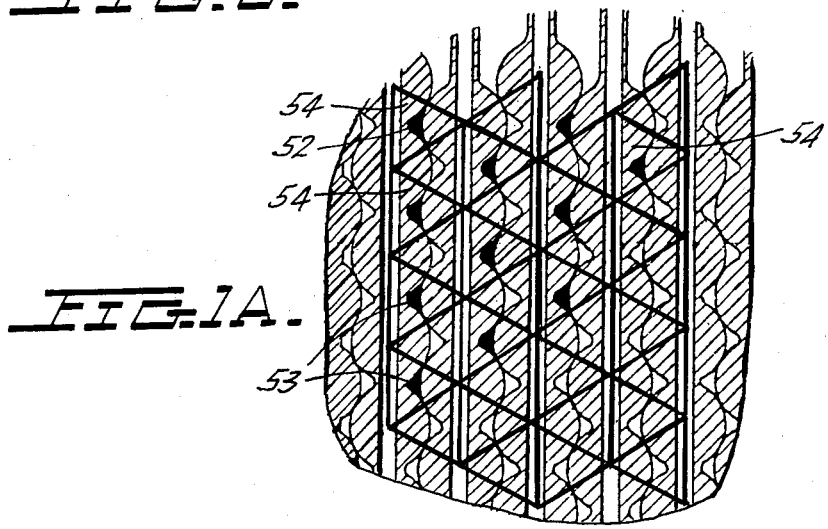
FIG. 1A is excised from FIG. 1 and will be used for explaining the first embodiment of the invention.

This is seen best in FIGS. 1A, 6 and 6A which illustrate diagrammatically the layer-to-layer internesting. In FIG. 1A, triangles 54 have been drawn around several of the spaces 52 and the nests 54. The spaces 52 were darkened to highlight them.

In FIG. 6 lines 58 point to the locations where lobes 36 of a first layer 56 will be wedged in the nests 53 of a second adjoining layer 57. The relative positions of layers 56 and 57 are illustrated in FIG. 6A.

A second embodiment for a tube arrangement is illustrated in FIGS. 5 and 5A, which comprises a modification to the embodiment of FIGS. 6 and 6A. Here, the spherical lobes 36 of adjacent tubes 32 in the same layer 59 are not offset or internested with one another. Instead, they are aligned so that each nest 53 is defined by four lobes 36. The lobes 36 of adjacent layers will fit into nests 53 as in the first embodiment. Again lines 58 are used to indicate the positions that will be occupied by the lobes 36 of one layer with respect to its adjacent layer. FIG. 5A shows two superposed layers in accordance with this embodiment.

A comparison of the first and second embodiments shows that in the first embodiment, more tubes 32 can fit in a single layer while in the second embodiment, due to the larger size of the nests 53, more layers can be packed in the chamber 30. However, it can be shown that both embodiments accommodate the same total numbers of lobes 36 and as a consequence have the same priming volume so that the benefits of the invention can be realized with either embodiment.

The unique tube packing of the first and second embodiments produce a labyrinth of interstitial spaces 62 of a unique and regular pattern. To maintain this regular pattern throughout the chamber 30, including at the boundary between the outermost tubes located adjacent to the interior surface 64 (FIG. 3) of the housing 12, the interior surface 64 is shaped to have spherical projections 60 which nests into the spaces between lobes which lie adjacent thereto.

The housing 12 is provided with an inlet manifold 66 located near first plate 22 and an outlet manifold 68 near the second plate 26. The medium to be treated is injected into an inlet port 70 of inlet manifold 66 under pressure whereas the medium, i.e. blood, spread throughout the manifold volume located under plate 22. From there, the medium flows into chamber 30 and spreading throughout interstitial spaces 62 it reaches the bottom of the chamber 30. From the output manifold 68 the blood exits through output port 72. As blood flows through the chamber 30, due to the unique pattern of interstitial spaces created within the chamber 30 by the internested spherical lobes 36, certain secondary flows are induced within the main blood flow. The above-mentioned secondary flows promote constant renewal of the zero velocity adjacent to the membrane layer of flow, and also stirring and mixing of blood which, on the one hand, make the mass exchanging process more efficient and, on the other hand, prevents clotting of the blood.

Due to smooth profile of the mass exchanging chamber and also absence of sharp turns on abrupt changes in the blood flow, the shear stresses in the flowing blood are minimized and, as a consequence, so is the blood trauma.

Also, because of the regularity of the pattern throughout the exchange chamber, the blood flow distribution is very even and uniform, which also makes the apparatus more efficient and prevents clotting.

The mass/heat exchange device of the present invention is usable for a variety of applications including blood oxygenation, dialyzing to replace or supplement kidney functions, heat exchange or similar tasks. Regardless of the actual use, the basic structure of the device remains the same, except that the material of which the tubular members 32 are constructed and its outer surface coating is selected to suit particular applications. Several contemplated applications are discussed below.

It has been noted that in blood oxygenators, oxygen is the treating medium and blood is the medium to be treated. In this case, the tubular members are formed of material which allows carbon dioxide to pass from the blood into the oxygen chamber while oxygen permeates through the tube body 44 into the blood.

The tubes 32 are comprised of microporous material which may include plastics such as Teflon ® (PTFE), polypropylene and other porous plastics. Ceramics or ceramic metals could also be used. In either case, the material will preferably have very small pore sizes, high porosity, and will be hydrophobic to assure that only gaseous matter passes back and forth while aggregates remain separated from one another.

Alternatively, pore sizes an order of magnitude larger may be used if the tubes are covered by membrane 36 illustrated in FIG. 4. The material of membrane 36 may be silicone elastomer, or any gas permeable material suitable for oxygenation. Membranes, such as membrane 36, having hydrophobic properties are useful for coating tubes comprised of hydrophilic materials.

For devices other than blood oxygenators, materials of suitable pore sizes and hydrolical properties are selected. In the case of a heat exchanger, the tube need not be permeable at all. Instead, it will comprise heat conducting metals or plastic impregnated by metal.

As noted, the shape of the tubes 32 and the tube-to-tube arrangement is designed to maximize the ratio of exchange surface to the total priming volume which is occupied by the medium to be treated. The calculations which follow are carried out with respect to the first embodiment of the invention and will show that the present invention produces a fourfold improvement over prior art embodiments wherein tubes of uniform outside diameter are used to provide an identical total exchange surface.

CALCULATIONS

With respect to the first embodiment, the following is defined:

$n_1$—number of spherical lobes in each tubular element $n_2$—number of tubular elements in each layer $n_3$—number of layers $l_1$—length of tubular elements $l_2$—width of each layer $l_3$—total thickness across all layers $V_H$—total internal volume of the housing $V_S$—volume occupied by all spherical lobes $A$—surface area of mass/heat exchange $V_O$—priming volume $D$—diameter of the spherical lobes $$l_1 = n_1 D$$
$$l_2 = n_2 D \cos 30°$$
$$l_3 = n_3 D \sqrt{2/3}$$
$$V_H = l_1 l_2 l_3 = D^3 n_1 n_2 n_3 \sqrt{1/2}$$
$$V_S = D^3 n_1 n_2 n_3 \pi/6$$
$$V_O = V_H - V_S = 0.184 n_1 n_2 n_3 D^3$$
$$A = \pi D^2 n_1 n_2 n_3$$

Applying the above equations, it follows that the total available exchange surface area per unit of priming volume satisfies the relationship $A/V_O = 17/D$ or $V_O = A \times D/17$ where $V_O$ is the priming volume and $A$ is the total surface area.

In a similar prior art device which uses straight cylindrical tubing of uniform outer cross-section having a diameter D and a total surface area A, the surface area per unit of priming volume would be $A/V_O' = 4/D$ or $V_O' = A \times D/4$. Thus, the priming volume $V_O$ of the present invention is proportional to D/17 while the priming volume $V_O$ of the prior art is D/4. Therefore, for identical oxygenation capacity without ever taking secondary flow into consideration, the device of the present invention reduces the priming volume by a factor of four.

Although the present invention has been described in connection with preferred embodiments thereof, many other variations and modifications will now become apparent to those skilled in the art. It is preferred, therefore, that the present invention be limited not by the specific disclosure herein, but only by the appended claims.

What is claimed is:

1. A mass/heat transfer apparatus, comprising:
   an enclosed housing having first and second opposite ends;
   a first plate in the housing adjacent the first end and a second plate in the housing adjacent the second end, the first and second plates dividing the interior of the housing into three chambers including a first and a second chamber which are adjacent, respectively, to the first and second ends of the housing, and a central chamber between the plates;
   a plurality of layers of mass exchanging material located in and filling the central chamber and sequentially abutting one another, each layer including a plurality of semi-permeable, substantially spherical lobes and the lobes in each said layer being so arranged that each group of adjacent lobes defines a lobe-holding nest, adjacent layers of said plurality of layers being positioned relative to one another such that substantially every one of the lobes is disposed in at least one respective nest which is located in the layers of lobes adjacent thereto;
   a plurality of passageways extending from the first to the second chamber, each passageway passing through the first and second plates and through a plurality of the lobes, each lobe having at least one of the passageways passing therethrough and the passageways being sealed from the central chamber; and
   a plurality of inlets and outlets at the housing including a treating medium inlet into the first chamber, a treating medium outlet from the second chamber, a medium to be treated inlet into the central chamber and a medium to be treated outlet from the central chamber.

2. The apparatus of claim 1 further comprising a respective semi-permeable membrane which covers an outer surface of each lobe, the membrane being sufficiently impervious to keep the treating and the to be treated mediums apart and sufficiently permeable to permit diffusion of particles to be transferred therethrough.

3. The apparatus of claim 1 in which the tubes are arranged in a predetermined regular manner in the central chamber.

4. The apparatus of claim 1 in which the housing is generally rectangularly shaped.

5. The apparatus of claim 1 in which the housing is cylindrically shaped having a longitudinal axis and the first and second ends thereof intersect the axis.

6. The apparatus of claim 1 in which the passageways extend generally in parallel to one another.

7. The apparatus of claim 6 in which the apparatus is a blood oxygenator whereby said treating medium is oxygen and said medium to be treated is blood.

8. The apparatus of claim 7 in which the ratio of the volume outside the lobes in the central chamber to the total surface area of the lobes varies as the diameter of the lobes divided by about seventeen.

9. The apparatus of claim 3 in which the layers of lobes are flat and parallel to one another.

10. The apparatus of claim 1 in which the apparatus is a blood oxygenator and wherein at least an outer surface of the tubes which is exposed within said central chamber as well as the surfaces of the housing exposed to the central chamber are comprised of blood compatible materials.

11. The apparatus of claim 10 in which the tubes comprise a microporous material suitable for blood oxygenation.

12. The apparatus of claim 11 in which the microporous materials comprise materials selected from microporous plastics, ceramics, and ceramic metals.

13. The apparatus of claim 10 in which the tubes comprise a microporous material having pore sizes larger than would be suitable for blood oxygenation and wherein the tubes are coated by a gas permeable and blood impermeable material.

14. The apparatus of claim 9 in which the apparatus is a dializer and wherein the tubes comprise semi-permeable, microporous materials which permit biological masses to pass between the central chamber and the interior of the tubes.

15. The apparatus of claim 9 in which the apparatus is a heat exchanger.

16. The apparatus of claim 9 in which the housing comprises an interior surface shaped to conform to tubes which are located adjacent thereto.

17. The apparatus of claim 9 further comprising a semi-permeable, blood compatible membranes for covering the tubes.

18. The apparatus of claim 17 in which the membranes comprise a material selected from porous plastics, ceramic and ceramic metal.

19. An apparatus as in claim 1, in which each layer of lobes comprises a plurality of elongated tubes extending between the first and second plates for allowing a treating medium to pass between the first and second chambers, each of said tubes forming a plurality of said spherical lobes which follow one another along said tube, said spherical lobes of each tube being defined by an outer surface of the tube havng the shape of said spherical lobes.

20. An apparatus as in claim 19, in which the lobes in any given one of said layers are aligned to one another so that every four adjacent lobes in the given layer define one of said lobe-holding nests.

21. An apparatus as in claim 19, in which the lobes in any given one of said layers are lengthwise offset from one another so that every three adjacent lobes in the given layer define one of said lobe-holding nests.

22. An apparatus as in claim 19, in which the plurality of the layers are arranged concentrically relative to one another.

23. An apparatus as in claim 19, in which the plurality of layers extend spirally relative to one another.

* * * * *